(12) United States Patent
Davenport et al.

(10) Patent No.: US 11,026,810 B2
(45) Date of Patent: Jun. 8, 2021

(54) PROSTHESIS ALIGNMENT SYSTEM

(71) Applicant: Biomet Manufacturing, LLC, Warsaw, IN (US)

(72) Inventors: Austen Davenport, Columbia City, IN (US); Kirk J Bailey, Rochester, IN (US); Nikole Becknell, Leesburg, IN (US); W. Jason Slone, Silver Lake, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 399 days.

(21) Appl. No.: 15/061,319

(22) Filed: Mar. 4, 2016

(65) Prior Publication Data

US 2016/0184109 A1    Jun. 30, 2016

Related U.S. Application Data

(63) Continuation-in-part of application No. 14/639,548, filed on Mar. 5, 2015, now Pat. No. 10,813,774.
(Continued)

(51) Int. Cl.
*A61F 2/46* (2006.01)
*A61F 2/30* (2006.01)
*A61B 17/56* (2006.01)

(52) U.S. Cl.
CPC ........ *A61F 2/4609* (2013.01); *A61F 2/30942* (2013.01); *A61F 2002/30566* (2013.01);
(Continued)

(58) Field of Classification Search
CPC . A61B 17/86; A61B 17/7068; A61B 17/8057; A61B 17/8605; A61B 17/8685; A61B 17/8872; A61B 17/0642; A61B 17/155; A61B 17/1742; A61F 2002/30841; A61F 2220/0016; A61F 2002/30538; A61F 2002/3055; A61F 2002/30601;
(Continued)

(56) References Cited

U.S. PATENT DOCUMENTS 5,540,697 A  *  7/1996  Rehmann ............... A61F 2/4609
                                                        294/95
5,571,111 A     11/1996  Aboczky
(Continued)

OTHER PUBLICATIONS

"U.S. Appl. No. 14/639,548, Non Final Office Action dated Nov. 30, 2017", 10 pgs.
(Continued)

*Primary Examiner* — Ann Schillinger
(74) *Attorney, Agent, or Firm* — Schwegman Lundberg & Woessner, P.A.

(57) ABSTRACT

An alignment plate can comprise a body having an exterior-facing surface and an implant-facing surface, at least one adjustable finger extending in a direction transverse to a plane defined by the body, and at least one patient-engaging surface positioned on the at least one adjustable finger. The adjustable finger can be adjustable to vary the distance between the patient-engaging surface and the implant-facing surface. The patient-engaging surface can be configured to engage a portion of a patient to align the alignment plate relative to the patient in a selected orientation. Additional apparatus, methods, and systems are disclosed.

20 Claims, 9 Drawing Sheets

Related U.S. Application Data

(60) Provisional application No. 62/128,217, filed on Mar. 4, 2015, provisional application No. 61/949,576, filed on Mar. 7, 2014.

(52) U.S. Cl.
CPC ............... *A61F 2002/4627* (2013.01); *A61F 2002/4629* (2013.01); *A61F 2002/4681* (2013.01); *A61F 2002/4687* (2013.01)

(58) Field of Classification Search
CPC ............ A61F 2002/30878; A61F 2/30; A61F 2/30756; A61F 2/32; A61F 2/4603
See application file for complete search history.

(56) References Cited

U.S. PATENT DOCUMENTS

| | | | |
|---|---|---|---|
| 5,879,402 A * | 3/1999 | Lawes | A61B 17/7098 128/898 |
| 6,027,505 A | 2/2000 | Peter et al. | |
| 6,395,005 B1 * | 5/2002 | Lovell | A61F 2/4657 606/91 |
| 7,179,259 B1 | 2/2007 | Gibbs | |
| 2012/0053592 A1 * | 3/2012 | Burgi | A61F 2/4609 606/91 |
| 2014/0276872 A1 * | 9/2014 | Song | A61F 2/4609 606/91 |
| 2015/0250614 A1 | 9/2015 | Davenport et al. | |

OTHER PUBLICATIONS

"U.S. Appl. No. 14/639,548, Restriction Requirement dated Sep. 1, 2017", 8 pgs.

"U.S. Appl. No. 14/639,548, Response filed Oct. 30, 2017 to Restriction Requirement dated Sep. 1, 2017", 7 pgs.

"U.S. Appl. No. 14/639,548, Response filed Mar. 26, 2018 to Non Final Office Action dated Nov. 30, 2017", 9 pgs.

"U.S. Appl. No. 14/639,548, Final Office Action dated Jul. 3, 2018", 9 pgs.

"U.S. Appl. No. 14/639,548, Response filed Aug. 20, 2018 to Final Office Action dated Jul. 3, 2018", 10 pgs.

"U.S. Appl. No. 14/639,548, Advisory Action dated Sep. 12, 2018", 3 pgs.

"U.S. Appl. No. 14/639,548, Non Final Office Action dated Nov. 14, 2018", 9 pgs.

"U.S. Appl. No. 14/639,548, Final Office Action dated Jul. 1, 2019", 10 pgs.

"U.S. Appl. No. 14/639,548, Response filed Apr. 12, 2019 to Non Final Office Action dated Nov. 14, 2018", 11 pgs.

"U.S. Appl. No. 14/639,548, Response filed Oct. 31, 2019 to Final Office Action dated Jul. 1, 2019", 11 pgs.

* cited by examiner

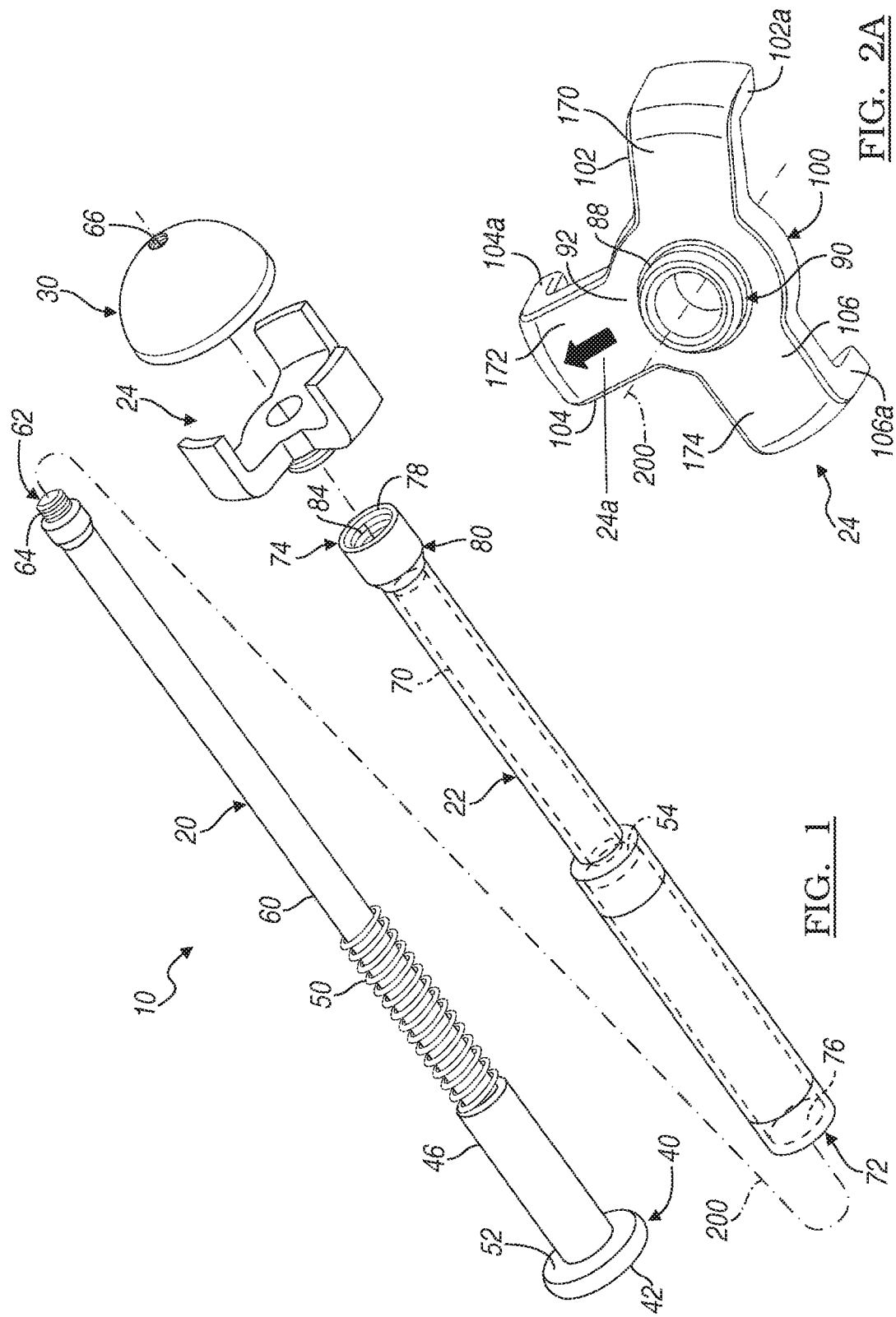

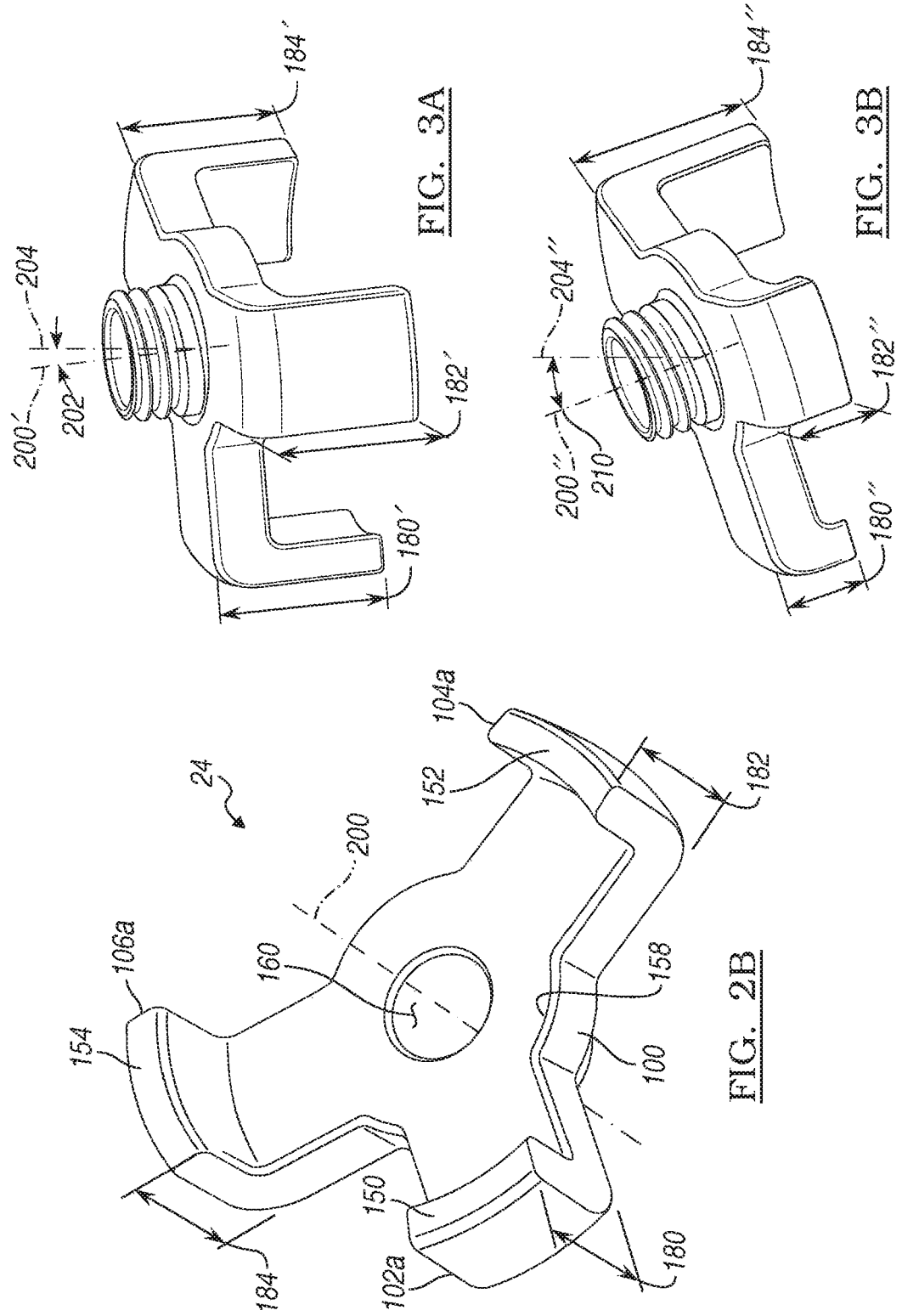

PROSTHESIS ALIGNMENT SYSTEM

CROSS-REFERENCE TO RELATED APPLICATIONS

This application claims the benefit of U.S. Provisional Application No. 62/128,217, filed on Mar. 4, 2015. This application is a Continuation-In-Part application of U.S. patent application Ser. No. 14/639,548, entitled "SUBJECT CONTACTING PLATE" filed on Mar. 5, 2015, which claims the benefit of U.S. Provisional Application No. 61/949,576 filed on Mar. 7, 2014 and U.S. Provisional Application No. 62/128,217, filed on Mar. 4, 2015. The entire disclosure of each of the above applications is incorporated herein by reference.

BACKGROUND

A prosthesis can be positioned in an anatomy, such as a human patient, for various purposes. For example, a prosthesis can be positioned to replace an articulating portion of an anatomy. Incorrectly reamed anatomy can result in incorrectly placed prosthesis. Incorrectly placed prostheses can result in pain, limit range of motion, increase wear debris, limit joint stability, and decrease the lifespan of the implant. In one particular example, an acetabular cup can be positioned in an acetabulum of a patient to replace damaged or diseased bone. Conventionally, a visual identification is used to align and confirm placement of the acetabular cup to correct for or to replicate anatomical geometries. Conventional systems and methods can result in misaligned implants, incorrect reaming depths, inefficiencies, or the like.

Overview

To better illustrate the instrument disclosed herein, a non-limiting list of examples is provided here:

In Example 1, an alignment plate can be provided that includes a body having an exterior-facing surface and an implant-facing surface, at least one adjustable finger extending in a direction transverse to a plane defined by the body, and at least one patient-engaging surface positioned on the at least one adjustable finger, the adjustable finger adjustable to vary the distance between the patient-engaging surface and the implant-facing surface, the patient-engaging surface configured to engage a portion of a patient to align the alignment plate relative to the patient in a selected orientation.

In Example 2, the alignment plate of Example 1 is optionally configured such that the selected orientation is predetermined based on image data of the patient.

In Example 3, the alignment plate of Example 1, further includes at least one threaded hole extending at least partially through the body, the at least one adjustable finger comprising a threaded member that is configured to threadably engage the at least one threaded hole to vary the distance between the patient-engaging surface and the implant-facing surface by rotation of the at least one adjustable finger in a clockwise direction or a counterclockwise direction.

In Example 4, the alignment plate of Example 3 is optionally configured such that the body includes a central region, and at least one arm extending radially outward from the central region, the at least one threaded hole extending at least partially through the at least one arm.

In Example 5, the alignment plate of Example 4 is optionally configured such that the at least one finger is adjustable in an orthogonal direction relative to the at least one arm.

In Example 6, the alignment plate of Example 1 is optionally configured such that the at least one adjustable finger includes at least three adjustable fingers.

In Example 7, the alignment plate of Example 1, further includes a through bore extending at least partially through the body and configured to receive a tool.

In Example 8, a system includes a rod extending from a first end to a second end, and an alignment plate configured to place an implant in a patient in a predetermined orientation, the alignment plate having a central region, a through bore extending at least partially through the central region, the rod configured to extend through the through bore, and at least one engaging surface spaced radially from the central region and adjustable in a direction transverse to the central region, the engaging surface configured to engage a portion of a patient to align the alignment plate and the rod relative to the patient.

In Example 9, the system of Example 8, further includes a sleeve member extending from a first end to a second end having a through bore extending through the sleeve member configured to slidably receive the rod, and the sleeve member further includes an alignment plate-engaging portion at the second end to hold the alignment plate relative to the sleeve member during movement of the rod.

In Example 10, the system of Example 9 is optionally configured such that the rod includes part of a reamer tool and the sleeve member includes a depth indicator.

In Example 11, the system of Example 8 is optionally configured such that the rod includes part of a reamer tool and the sleeve member includes a depth stop instrument to prevent the reamer tool from reaming beyond a selected depth.

In Example 12, the system of Example 11 is optionally configured such that the depth stop instrument is adjustable to allow for a variety of selected depths.

In Example 13, the system of Example 8, further includes at least one adjustable finger extending radially from the central region, the at least one adjustable finger adjustable to vary the distance between the at least one engaging surface and the central region in the direction transverse to the central region.

In Example 14, the system of Example 13 is optionally configured such that the at least one adjustable finger includes at least three adjustable fingers, the at least one engaging surface includes at least three engaging surfaces, each of the at least three fingers has at least one of the engaging surfaces, and each of the engaging surfaces is configured to selectively engage a portion of the patient during positioning of an implant with the rod.

In Example 15, a system for placing a prosthetic member includes a rod extending from a first rod end to a second rod end, a sleeve extending from a first sleeve end to a second sleeve end having a through bore extending through the sleeve configured to slidably receive the rod member, and an alignment plate having a through bore through which the rod is configured to extend, a first arm and a second arm both extending from a central region through which the through bore extends, a first finger including a first patient-engaging surface configured to be spaced by a first distance in a transverse direction from the first arm, and a second finger including a second patient-engaging surface configured to be spaced a first distance in a transverse direction from the second arm, the first distance and the second distance selected to achieve a preselected alignment of at least one of the rod or the sleeve when the sleeve is engaged to the alignment plate and the first adjustable patient-engaging surface and the second adjustable patient-engaging surface are engaging the subject.

In Example 16, the system of Example 15 is optionally configured such that the sleeve further includes an alignment plate-engaging portion at the second end to hold the alignment plate relative to the sleeve member during movement of the rod, the rod configured to slide relative to the alignment plate.

In example 17, the system of Example 15 is optionally configured such that the alignment plate further includes a third arm extending from the central region is optionally configured such that the third arm is spaced a distance from each of the first and second arms around the central region, and a third adjustable patient-engaging surface configured to be positioned a third distance in a transverse direction from the third arm.

In example 18, the system of Example 15 is optionally configured such that the first finger extends between the first arm and the first adjustable patient-engaging surface, and the second finger extends between the second arm and the second adjustable patient-engaging surface.

In example 19, the system of Example 18 is optionally configured such that the first finger is configured to move the first adjustable patient-engaging surface closer to and further from the first arm, and the second finger is configured to move the second adjustable patient-engaging surface closer to and further from the second arm.

In example 20, the system of Example 19 is optionally configured such that the first finger includes a first threaded member configured to engage a first threaded hole extending through the first arm, and the second finger includes a second threaded member configured to engage a second threaded hole extending through the second arm.

In Example 21, the apparatus, system, or method of any one or any combination of Examples 1-20 can optionally be configured such that all elements or options recited are available to use or select from.

These and other examples and features of the present devices, systems, and methods will be set forth in part in the following Detailed Description. This overview is intended to provide a summary of subject matter of the present patent application. It is not intended to provide an exclusive or exhaustive removal of the invention. The detailed description is included to provide further information about the present patent application.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various examples discussed in the present document.

FIG. 1 is an exploded view of an alignment system, in accordance with at least one example of the present disclosure.

FIG. 2A is a top view of an alignment plate, in accordance with at least one example of the present disclosure.

FIG. 2B is a bottom view of an alignment plate, in accordance with at least one example of the present disclosure.

FIG. 3A is a plan view of a first configuration of an alignment plate to achieve a first orientation, in accordance with at least one example of the present disclosure.

FIG. 3B is a plan view of a second configuration of an alignment plate to achieve a second orientation, in accordance with at least one example of the present disclosure.

DETAILED DESCRIPTION

Figure 4:
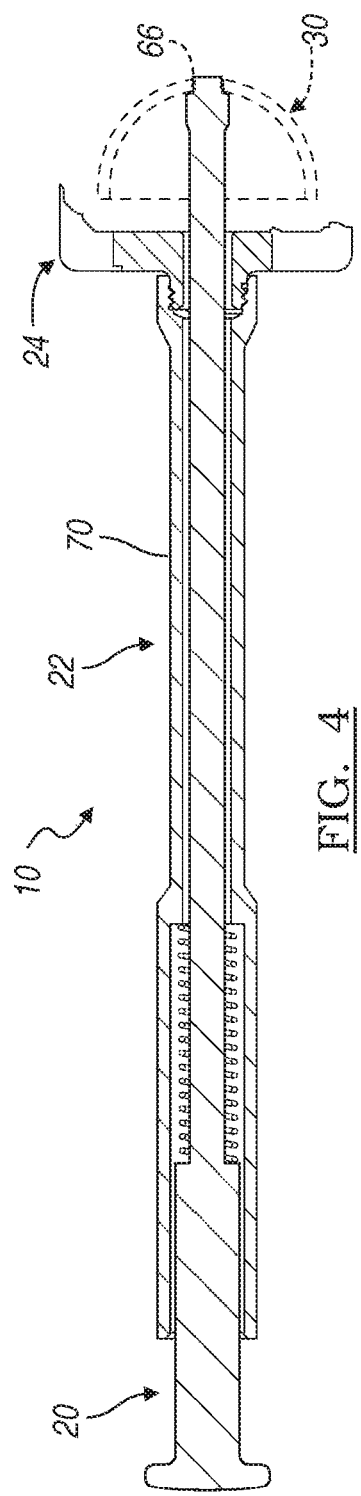
FIG. 4 is an assembled cross-sectional view of the alignment system, in accordance with at least one example of the present disclosure.

A system can be used to position a member relative to a substrate or positioning a member based upon predetermined and preselected orientations. For example, an acetabular cup can be positioned within an acetabulum at a preselected and predetermined orientation, such as to achieve a selected biomechanical geometry and range of motion. It is understood, however, that a member can be positioned relative to any substrate or receiving structure, such as an aircraft, a mounting plate, a casing, or any other appropriate receiving member. Generally, an alignment member can be designed and formed to include a selected geometry that will mate complementarily with a geometry of a substrate to guide an implanting or positioning member through a rod and an alignment plate.

According to various embodiments, an alignment plate can be designed and formed based upon a known geometry of a subject, such as a human patient. The alignment plate can include various members, such as a plurality of fingers or legs, to contact the selected points of the anatomy. Based upon contact of the fingers at the selected points of the anatomy, the alignment plate can be aligned at a preselected or predetermined alignment with a portion of the anatomy, such as an acetabulum. Once the plate is aligned, an acetabular cup can be impacted into the acetabulum at the preselected and predetermined geometry to achieve a predetermined and preselected alignment and placement of the acetabular cup.

Further areas of applicability will become apparent from the description provided herein. The description and specific examples in this summary are intended for purposes of illustration only and are not intended to limit the scope of the present disclosure.

According to various examples an implantation assembly 10 can include an impaction rod 20, an impaction sleeve 22, and an alignment plate 24. The assembly of the impaction rod 20, the impaction sleeve 22, and the alignment plate 24 may be used to position and implant a prosthesis, such as an acetabular prosthesis 30, into an acetabulum, as discussed further herein. Generally, the acetabular cup 30 can be interconnected with the impaction rod 20, as discussed further herein, to be positioned into a selected anatomy. After positioning of the acetabular cup 30 into the anatomy, the impaction rod 20 can be disconnected from the acetabular cup 30 and the implantation assembly 10 can be removed from the acetabular cup 30 and the selected patient to allow for completion of a procedure.

According to various examples, the impaction rod 20 can include an impaction head or portion 40 that has an impaction surface 42 that can be struck or impacted with a selected implement, such as a mallet 44 (FIG. 4). The impaction rod 20 can have the impaction head 40 interconnected with a first section 46 that can have a selected diameter that is equal to, less than, or greater than a diameter of the impaction head 40. In at least one example, the impaction head 40 can extend in a radial direction beyond the first rod section 46 to allow for a large surface area for receiving the impaction mallet 44 (see FIG. 5).

Further, according to various examples, a spring 50 can be positioned near the first section 46 and to contact a second surface or spring surface 52 of the first section or the impaction head 40. The spring 50 can engage a ledge or wall 54 within the impaction sleeve 22. The spring 50, when engaging the ledge 54, can hold the impaction rod 20 in a selected position relative to the impaction sleeve 22. Further, the spring 50 can act as a rebound spring to position the impaction rod 20 at a distance away from the impaction sleeve 22 or the alignment plate 24 in at least an initial position of the impaction rod 20 relative to the alignment plate 24 and a selected anatomy.

The impaction rod 20 may further include a second section 60 that extends from the first section 46. The second section 60 can include a diameter that is the same as or different than the first section 46, such as larger or smaller in diameter to the first section 46. The second section 60 extends from the first section 46 and may terminate in a prosthesis or acetabular cup-engaging portion 62. The acetabular cup-engaging portion 62 can include an externally threaded portion that includes external threads 64 that may engage internal threads 66 in the acetabular cup 30. The internal thread 66 can be generally known threads in an apical hole, such as threads included in the G7™ acetabular cup system and/or the Ringloc® acetabular cup system, sold by Biomet, Inc., having a place of business in Warsaw, Ind. The implant or cup-engaging region 62, therefore, can be generally similar to or identical to generally known cup-engaging regions.

The alignment sleeve 22 can be formed to align or position the impaction rod 20 relative to the acetabular cup 30. For example, the alignment sleeve 22 can include an internal bore 70 through which the impaction rod 20 is configured to pass. The internal diameter of the internal bore 70, therefore, can include an internal diameter that can slidably engage the impaction rod 20. The internal diameter of the internal bore 70 can allow for space between the impaction rod 20 and a wall that defines the internal bore 70 and need not include a tight or contacting fit. In other words, the rod 20 can freely pass through the sleeve 22 for engaging the acetabular cup 30, as discussed herein. Generally, the impaction sleeve 22 can include a first or proximal end 72 through which the impaction rod 20 can initially pass to a second or distal end 74. The proximal end 72 can include an opening 76 to the internal bore 70 through which the impaction rod 20 can pass. The second end 74 can include a second opening 78 through which at least the cup connection region 62 can pass to engage the acetabular cup 30 through the alignment plate 24.

Formed near or at the second end 74 can be an alignment plate-engaging region or section 80. The alignment plate-engaging region 80 can include internal thread or any other appropriate connection portion 84 to engage the alignment plate 24. In various examples, the alignment plate-engaging portion can include a taper connection, a snap ring, a bayonet slot connection, etc. As illustrated, the internal thread 84 can engage an external thread 88 on a sleeve-engaging region 90 of the alignment plate 24, as further illustrated in FIG. 2A. The external thread 88 can threadably engage, such as by rotation, the internal thread 84 of the alignment sleeve 22 to hold the alignment plate 24 relative to and fixed to the alignment rod 20 for a selected procedure. A terminal or external surface of the second end 74 can engage the alignment plate 24, such as a top or exterior facing surface 92 of the alignment plate 24, to ensure an appropriate, known, and preselected position alignment of the alignment plate 24 relative to the alignment rod 20. For example, the connection of the alignment plate 24 to the sleeve 22 can ensure that at least the top surface 92 of the alignment plate 24 is orthogonal to a long axis of the sleeve 22.

With continuing reference to FIG. 1 and additional reference to FIGS. 2A and 2B, the alignment plate 24 can be held to the alignment sleeve 22 for a selected procedure, such as implanting or positioning the acetabular cup 30. According to various examples, the alignment plate 24 can include a central hub region 100 from which the sleeve-engaging section 90 can extend to engage the alignment sleeve 22. It is understood, however, that the alignment plate 24 can include a female or negative receiving or engaging region to engage in alignment sleeve 22. Accordingly, a positive or extending region 90 is not required to extend from the hub portion 100.

Further, according to various examples, one or a plurality of engaging legs or fingers 102, 104 and 106, can extend from the central hub region 100. Although illustrated are three fingers 102-106 included with the alignment plate 24, having three fingers is not a requirement. For example, less than or more than three fingers may be selected or included. As discussed herein, the number of fingers can be selected during a design and manufacture process based on design criteria, such as patient matching.

Extending away from the central hub 100, and generally directed away from the sleeve-engaging portion 90, may be tabs 102a, 104a, and 106a that extend at an angle from the respective fingers 102-106 and generally away from the alignment sleeve 22. As discussed further herein, the respective tabs 102a-106a can engage selected portions of the anatomy to ensure appropriate alignment of the alignment plate 24 relative to the selection portion of the anatomy. Through connection of the alignment sleeve 22 with the alignment plate 24 appropriate alignment of the alignment sleeve 22 and the impaction rod 20 are achieved. Accordingly, the plurality of fingers 102-106 and the plurality of tabs 102a-106a can be used to ensure appropriate alignment of the alignment sleeve 22 and the alignment impaction rod 20 with the selected anatomy to ensure positioning of the acetabular cup 30 in the anatomy in an appropriate and preselected alignment and position.

With continued reference to FIGS. 1 and 2A, and additional reference to FIG. 2B, the alignment plate 24 can include the three tabs 102a, 104a, and 106a. Each of the tabs 102a-106a can terminate in respective bone contacting surfaces 150, 152, and 154. Each of the bone contacting surfaces 150-154 can extend away from a bottom surface or implant-facing surface 158 of the central hub 100. A through bore 160 may be formed through the sleeve-engaging portion 90 and the bottom surface 158 to allow the impaction rod 20 to engage the acetabular cup 30, as discussed further herein.

Figure 5:
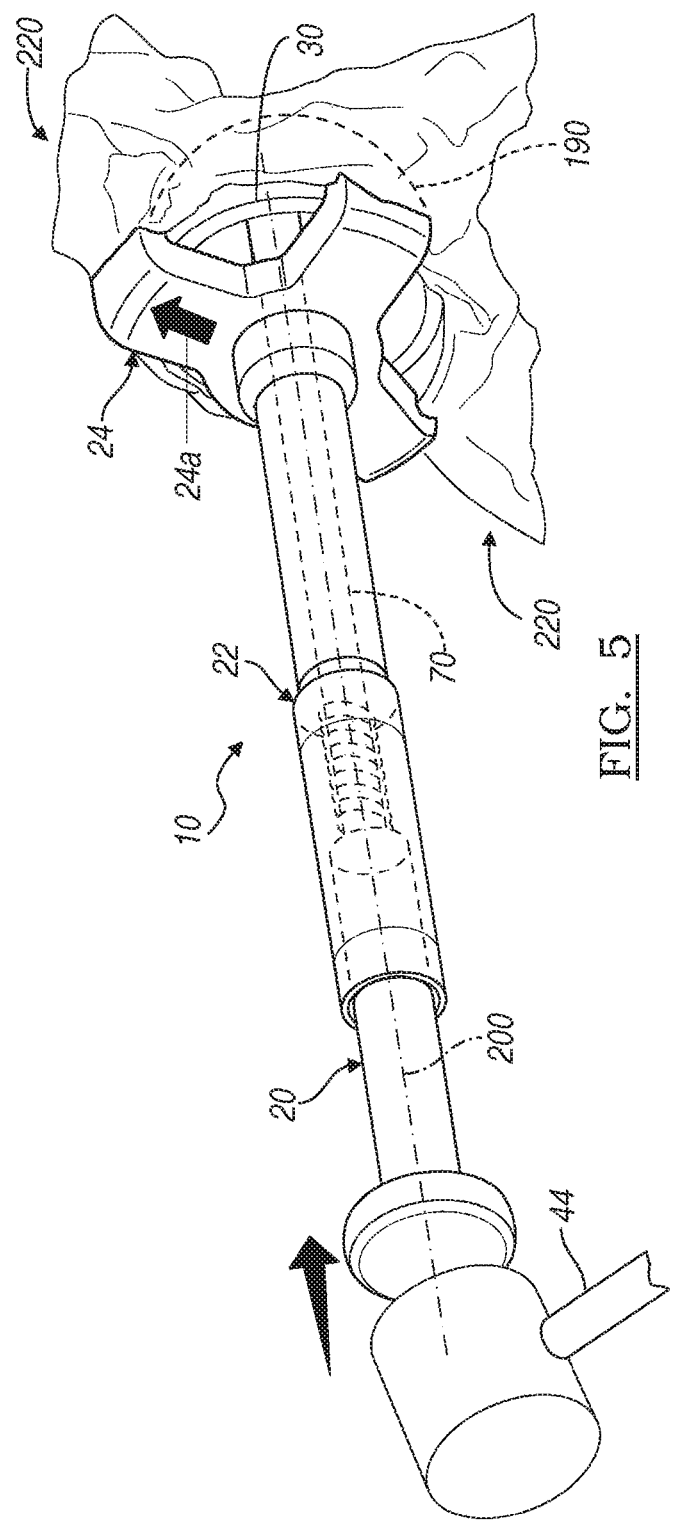
FIG. 5 is an environmental view of the alignment system, in accordance with at least one example of the present disclosure.

Each of the bone contacting surfaces 150-154 that are at a bottom or terminus of the respective tabs 102a-106a can extend a selected distance from a respective top surface 170, 172, 174 of each of the respective fingers 102-106 (as illustrated in FIG. 2A). For example, the first bone contacting surface 150 can extend a distance 180 from the upper surface 170 of the alignment plate 24. The second bone contacting surface 152 can extend a distance 182 from the upper surface 172 of the alignment plate 24. The third bone contacting surface 154 can extend a distance 184 from the upper surface 174 of the alignment plate 24. Each of the respective distances 180-184 can be determined and preselected based upon boney portions of an anatomy, such as boney portions adjacent or near an acetabulum 190 (as illustrated in FIG. 5). The boney portions can be selected to be spaced about the acetabulum 190 such as at a position to stabilize the alignment plate 24 during implantation and impaction of the acetabular cup 30. For example, the boney prominences or high points may be positioned at or near the ilium, the pubis, and the ischium. As illustrated in FIG. 2A and FIG. 5 an indicator 24a can be provided to assist in at least initial alignment and/or placement of the plate 24 relative to the anatomy. For example, the indicator 24a can include an arrow that is to be pointed towards the iliac crest when properly aligned. The boney portions that are contacted by the bone contacting surfaces 150-154, however, can be at any appropriate portion near the acetabulum 190 and above are merely examples.

The selected distances 180-184 can be selected based upon an appropriate or selected orientation, including a version angle of the cup 30, relative to the acetabulum 190 of the sleeve 22 and the impaction rod 20 during impaction of the acetabular cup 30 into the acetabulum 190. As is understood, the three distances 180-184 will orient an axis 200 that extends through the assembly 10 (including the assembled impaction rod 20, sleeve 22, and alignment plate 24) and the acetabular cup 30 when the bone contacting surfaces 150-154 contact the bone portion adjacent to the acetabulum 190. Accordingly, an orientation of the axis 200 relative to the acetabulum 190 can be selected and achieved based upon the respective distances 180-184. Further, the orientation and angle of the axis 200 can be preselected based upon an analysis and selected orientation of the acetabular cup 30 in the acetabulum 190.

The orientation of the axis 200 relative to the acetabulum 190 may be preselected based on various selections, such as anatomical geometry, desired range of motion after implantation, or intended orientation of the acetabular cup 30 relative to the acetabulum 190. The orientation may be achieved with appropriate mechanisms, such as review and analysis of image data of the acetabulum 190 prior to a procedure. For example, various procedures and systems can obtain image data of portions of an anatomy, such as a computer tomography (CT) Scan, a magnetic resonance image (MRI) scan, a plurality of two-dimensional images, and the like of a patient for determining a post-implantation orientation of an acetabular cup 30 relative to the acetabulum 190.

According to various examples, a user, such as a surgeon may determine the selected angle of the sleeve 22 and/or rod 20. A manufacturer of the plate 24 may then determine the lengths 180-184 to achieve the selected angle. It is further understood, that in at least one example, the user provides to the manufacturer only a selected final implantation orientation of the cup 30 and the manufacturer then analyzes the image data to determine the required angle of the sleeve 22 and/or rod 20 and then the required lengths 180-184. Thus, in such an example, the user need not determine manufacturing specifications, but can simply provide to a manufacturer a desired or selected final implantation orientation of the selected prosthesis.

As an example, and not to limit the appropriate or selectable lengths 180-184, FIGS. 3A and 3B illustrate two variations of the axis 200 relative to a perpendicular line 204. For example, as illustrated in FIG. 3A, the plate 24 can include distances 180'-184' such that the axis 200' is at a first angle 202 relative to the perpendicular line or axis 204. The angle 202 can be an appropriate angle, such as about 2°. With reference to FIG. 3B, the distances 180-184 are illustrated as 180"-184". The distance 184" can be greater than the distance 184' such that the axis 200" is at an angle 210 relative to the perpendicular line 204. The angle 210 may be greater than the angle 202, such as about 7°-10°. Accordingly, based upon analysis and selection by a user, such as a surgeon, the appropriate or implanted angle of the acetabular cup 30 can be selected and then achieved by selecting lengths 180-184 of the alignment plate 24 to achieve the selected angle.

According to various examples, the alignment plate 24 can be designed, manufactured, and produced based upon a selected individual patient. Accordingly, each patient can have the patient's own specific or patient-specific alignment plate 24 to achieve an appropriate alignment of the axis 200 relative to the acetabulum 190 of the specific patient. Appropriate alignment of the axis 200 can be achieved based upon analysis of the image data. According to various examples, the analysis can be achieved by analysis of image data, such as similar to the Signature™ patient matched system offered by Biomet, Inc. and/or the systems and methods as discussed in U.S. Patent App. Pub. No. 2011/0166578; 2011/01980899; or 2011/0015639; or U.S. Pat. No. 8,407,067 or 8,070,752, incorporated herein by reference.

The plate 24, therefore, including the lengths 180-184 may be designed after analysis of a patient, such as analysis of image data. The analysis and the desired angle can be determined and the plate 24 may be designed to achieve the alignment of the system 10 for implantation of the cup 30. Thus, the plate 24 may be manufactured after the analysis and determination of the desired and selected angle. Accordingly, each plate 24 may be designed and manufactured for substantially a single use with a specific procedure, such as a single patient.

The manufacture of the plate 24 may be performed in any appropriate manner. For example, a rapid prototyping or three-dimensional printing may be used to form the plate 24. Also, the plate 24 may be made of a polymer material that may efficiently and quickly molded into a selected shape, such as with injection molding. Moreover, the plate 24 may be machined, such as with a controlled machining, to achieve the selected dimensions to achieve the selected alignment.

With additional reference to FIGS. 4 and 5, the implantation assembly 10 can be assembled such that the impaction rod 20 is passed through the sleeve 22, such as passing the impaction rod 20 through the internal bore 70 of the sleeve 22 and through the alignment plate 24 to engage the apical thread 66 of the acetabular cup 30, as illustrated in FIG. 4. The alignment plate 24 may be threaded onto the sleeve 22 prior to passing the impaction rod 20 through the sleeve 22 to engage the acetabular cup 30. Accordingly, as illustrated in FIG. 4, the assembly can include the sleeve 22 attached to the alignment plate 24 and the impaction rod 20 attached to the acetabular cup 30. The rod 20 may be attached to the acetabular cup 30 after the assembly of the sleeve 22 to the alignment plate 24 and passing the rod 20 through the sleeve 22 and plate 24.

Once assembled, as illustrated in FIG. 5, the alignment plate 24 can engage the selected boney portions of a pelvis 220 near or adjacent to the acetabulum 190. The alignment plate 24 can align the axis 200 as preselected or predetermined by engaging the boney portions adjacent to the acetabulum 190. As noted above, the indicator 24*a* may be provided and/or used to assist in at least initial alignment of the plate 24 with the pelvis 220 and the selected boney portions. For example, the indicator 24*a* may be the arrow that is to be pointed towards the iliac crest when the plate 24 is aligned properly. The bone-engaging surfaces contacting the boney portions will align the axis 200 relative to the acetabulum 190 as preselected prior to the procedure and the acetabular cup 30 is appropriately aligned within the acetabulum 190 prior to impaction of the acetabular cup 30 into the acetabulum 190.

Once appropriately aligned, the mallet 44 may be used to engage in a selected manner, such as a forceful manner, the impaction rod 20. By impacting the impaction rod 20, the acetabular cup 30 will be engaged into the acetabulum 190. It is understood that various acetabular cups can be impacted into the acetabulum 190, such as substantially cementless acetabular cups. It is further understood, however, that various cements can be positioned in the acetabulum 190 prior to impaction. It is understood, therefore, that the cup 30 may be held in the acetabulum by a cement material and impaction with the mallet 44 may not be required. In a cemented system, the cup 30 may be placed in a cement mantle and the system 10 may be used essentially to ensure only appropriate and selected alignment rather than also providing the rod 20 for a forceful impaction of the cup 30.

Accordingly, once the acetabular cup 30 is implanted, such as by placement and/or impaction in the acetabulum, the impaction rod 20 can be disengaged from the acetabular cup 30 such as by unthreading the impaction rod 20 from the acetabular cup 30. Once the impaction rod 20 is unthreaded from the acetabular cup 30, the sleeve 22 and the alignment plate 24 are free to be removed from contact with the pelvis 220. Accordingly, the acetabular cup 30 may be implanted in a preselected alignment and orientation within the acetabulum 190 based upon the distances 180-184 as discussed above.

Figure 6:
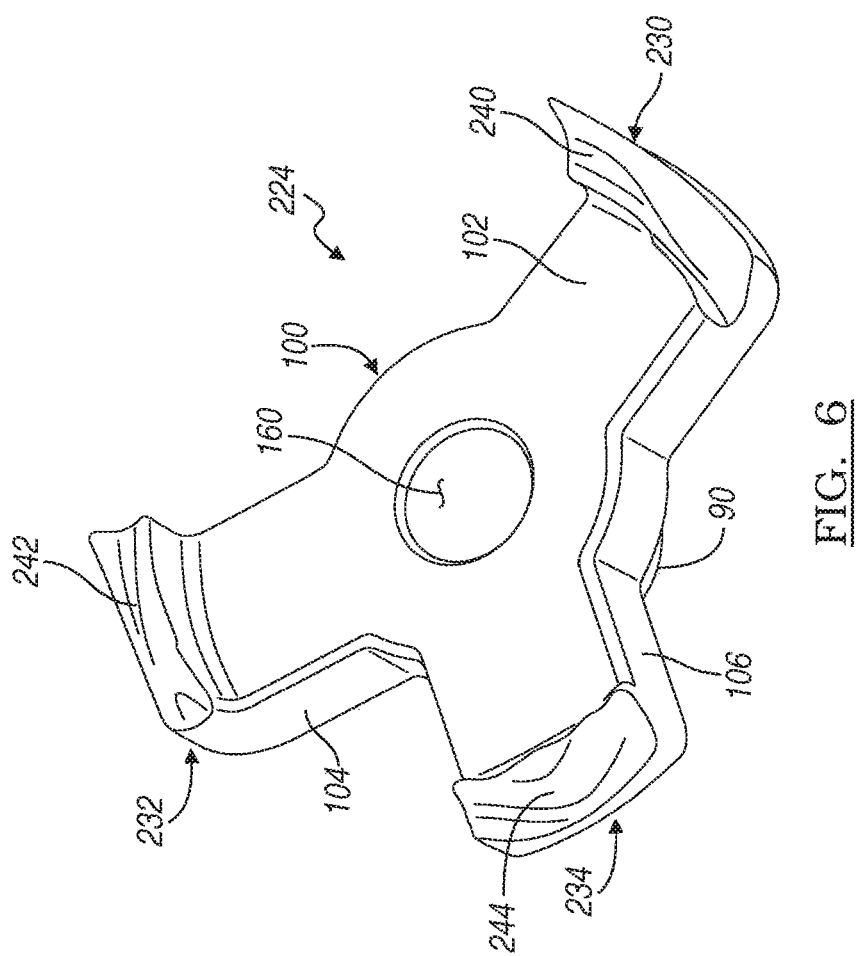
FIG. 6 is a bottom view of an alignment plate, in accordance with at least one example of the present disclosure.

According to various examples, with reference to FIG. 6, an alignment plate 224 is illustrated. The alignment plate 224 can be substantially similar to the alignment plate 24 discussed above, and include the central hub 100, the sleeve-engaging portion 90, the one or more fingers 102-106, and the through bore 160. The alignment plate 224 can differ from the alignment plate 24 in the configuration and design of bone-engaging surfaces.

As discussed above, tabs may extend from each of the fingers 102-106. For example, a first tab 230 can extend from the finger 102, a second tab 232 can extend from the second finger 104, and a third tab 234 can extend from the third finger 106. Each of the tabs 230-234 include substantially patient-specific bone-engaging surfaces 240, 242, and 244, respectively. Each of the patient-specific bone-engaging surfaces 240-244 can engage such portions of the anatomy, such as boney protrusions or high points on the pelvis 220 near the acetabulum 190 similar to the bone-engaging surfaces 150-154.

The patient-specific bone-engaging surfaces 240-244, however, include contours, shapes, and the like that are substantially complementary or mirror images of the bone portions of the pelvis 220. Forming such patient-specific geometries of the bone-engaging surfaces 240-244 can include obtaining image data of the patient and subtracting from the dimensions of the tabs 230-234 the geometry of the bone. Thus, the patient-specific bone-engaging surface 240-244 will engage substantially only a single and unique portion of the anatomy of a single patient. This can assist in reducing time in performing a procedure as the plate 24 will only fully engage and seat against the pelvis 220 in a single orientation.

The geometry of the alignment plate 224, however, can be altered including selecting or adjusting heights or distances of the bone-engaging surfaces 240-244 from respective top surfaces of the alignment plate 224 to achieve alignment as discussed above. The specific engagement of the patient-specific bone-engaging surfaces 240-244, however, can also help ensure that the alignment plate 224 is positioned at the specified and predetermined orientation relative to the anatomy.

It is understood that the bone engagement surfaces 240-244 can engage other hard portions of the anatomy that are not bone, such as cartilage, calcified regions, spurs, and the like. Further, the bone engagement surfaces 150-154 can similarly engage non-bone portions of the anatomy as selected to achieve an appropriate alignment. Thus, the bone contacting surfaces, according to the various examples, can engage any appropriate portion of the anatomy near the acetabulum to achieve the selected alignment of the system 10.

Accordingly, as discussed above, the positioning assembly 10 can be used to position an implant, such as the acetabular prosthesis 30 relative to the anatomy, including the acetabulum 190. It is understood that the assembly 10, however, can be used to position any appropriate prosthesis, such as a femoral head prosthesis, femoral stem prosthesis, humeral head prosthesis, glenoid prosthesis, or other appropriate prostheses. The alignment plate 24, 224 can be designed and manufactured with bone-engaging or hard surface-engaging portions to achieve an alignment of the sleeve 22 and the impaction rod 20 to implant the prosthesis in any appropriate manner. Accordingly, it is understood, that although discussed above is an exemplary instrument assembly to implant an acetabular prosthesis that appropriate prostheses can be implanted with the assembly 10 in an appropriate manner as understood by one skilled in the art.

Figure 7:
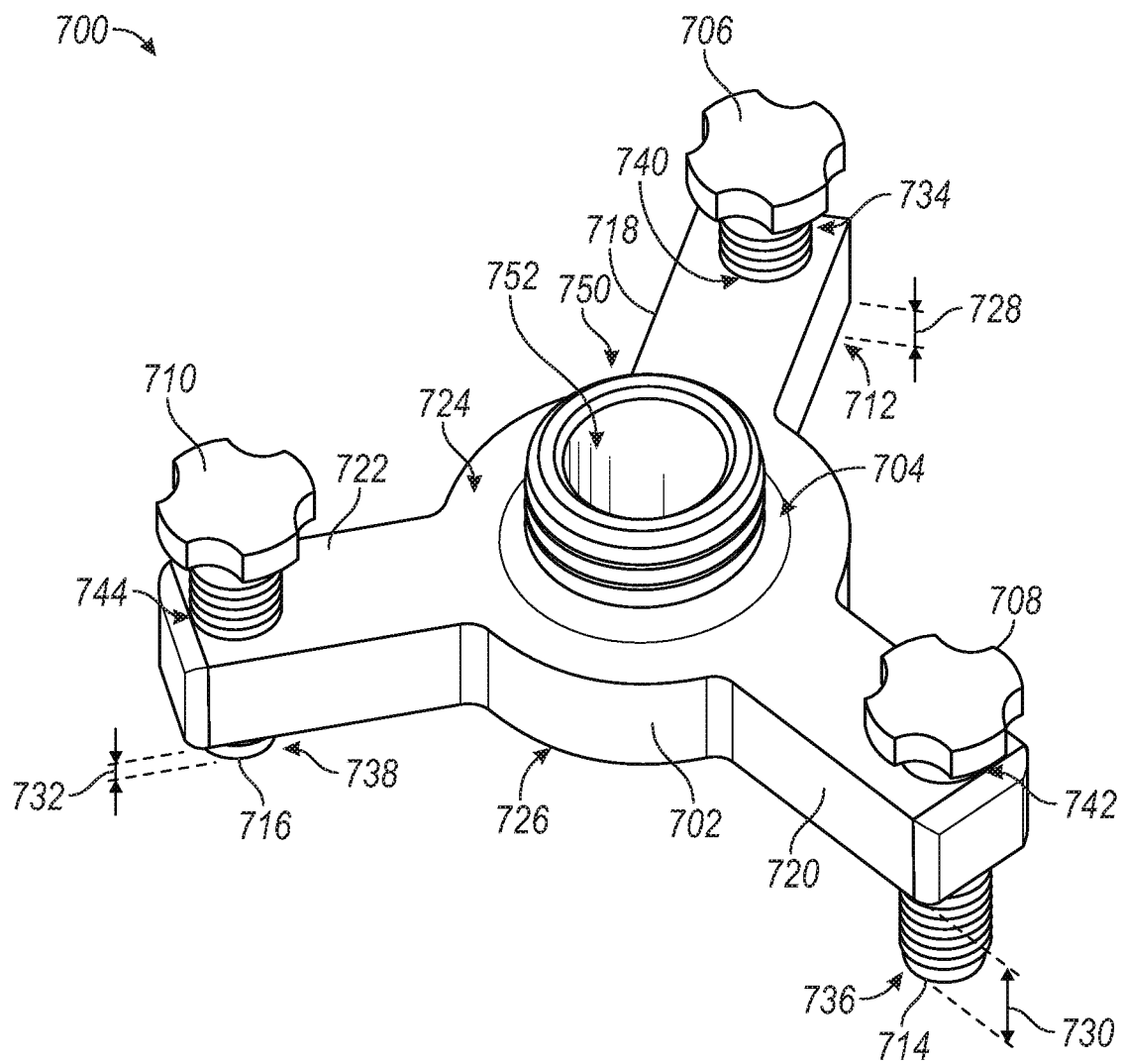
FIG. 7 is a plan view of an alignment plate, in accordance with at least one example of the present disclosure.

FIG. 7 is a plan view of an alignment plate 700, in accordance with at least one example of the present disclosure. The alignment plate 700 can include a body 702 having a central region 704 (or central portion, or central hub), one or more fingers 706, 708, 710, and one or more patient-engaging surfaces 712, 714, 716. In some examples, one or more arms 718, 720, 722 can extend radially outward from the central region 704 to the one or more fingers 706, 708, 710. In at least one example the arms can be spaced radially about the central region 704. In some examples, the central region 704 can include a sleeve-engaging portion 750, which can be threaded or otherwise configured to be coupled to a sleeve. In at least one example, the alignment plate 700 can be formed integral with the sleeve. In some examples, a through bore 752 can extend at least partially through the central region 704 and can be configured to receive a rod, such as an impaction rod or a reaming tool rod. In at least one example, the through bore 752 can extend at least partially through the sleeve-engaging portion 750.

In some examples, the one or more adjustable fingers 706, 708, 710 can extend in a direction transverse to a plane defined by the body 702. In at least one example, the one or more patient-engaging surfaces 712, 714, 716 can be positioned on the one or more adjustable fingers 706, 708, 710. In some examples, the one or more fingers 706, 708, 710 can be adjustable in an orthogonal direction relative to the one or more arms 718, 720, 722. In at least one example, the one or more patient-engaging surfaces 712, 714, 716 can be spaced radially from the central region and adjustable in a direction transverse to the central region. In at least one example, each of the patient-engaging surfaces 712, 714, 716 can be configured to selectively engage a portion of the patient during positioning of an implant with a rod.

The body 702 can generally include an exterior-facing surface 724 and an implant-facing surface 726. In some examples, one or more of the fingers 706, 708, 710 can be adjustable to vary a distance 728, 730, 732 between the patient-engaging surface 712, 714, 716 and the implant-facing surface 726. As such, the adjustable fingers 706, 708, 710 can be adjustable such that each of the patient-engaging surfaces can engage a portion of a patient to align the alignment plate 100 relative to the patient in a selected orientation. In at least one example, the selected orientation can be predetermined based on image data of the patient. In some examples, each of the distances 728, 730, 732 can be configured to be different from each other. In at least one example, one or more of the distances 728, 730, 732 can be configured to be the same as at least one other of the distances 728, 730, 732. In some examples, the distances 728, 730, 732 can be selected to achieve a preselected alignment of at least one of a rod or a sleeve when the sleeve is engaged to the alignment plate and the patient-engaging surfaces 712, 714, 716 are engaging the subject.

In the illustrated example, the adjustable fingers 706, 708, 710 can comprise bolts having threads 734, 736, 738, and the arms 718, 720, 722 can comprise corresponding threaded holes 740, 742, 744. The adjustable fingers 706, 708, 710 can be configured to threadably engage the threaded holes 740, 742, 744 to vary the distance 728, 730, 732 between the patient-engaging surfaces 712, 714, 716 and the implant-facing surface 726 by rotation of the adjustable finger in a clockwise direction or a counterclockwise direction. In at least one example, the adjustable fingers 706, 708, 710 can be configured to move the patient-engaging surfaces 712, 714, 716 closer to and further from the arms 718, 720, 722.

While the illustrated example depicts the adjustable fingers 706, 708, 710 as bolts, in other examples, the adjustable fingers 706, 708, 710 can comprise any of a variety of adjustable mechanisms to vary the distances 728, 730, 732 of the patient-engaging surfaces 712, 714, 716. While the illustrated example depicts the patient-engaging surfaces 712, 714, 716 as integral with the adjustable fingers 706, 708, 710, in other examples, the patient-engaging surfaces 712, 714, 716 can comprise a separate element coupled to the adjustable fingers 706, 708, 710. In at least one embodiment, each patient-engaging surface 712, 714, 716 can be removably coupled to the adjustable finger 706, 708, 710. While the illustrated example depicts arms 718, 720, 722, in some examples, the fingers 706, 708, 710 can extend from the body 702 rather than the arms. In at least one example, the arms 718, 720, 722 can be adjustable to vary a diameter of the alignment plate 700 to accommodate different implant diameters, or otherwise.

In some examples, the patient-engaging surfaces 712, 714, 716 can comprise a substantially patient-specific bone-engaging surface. That is, the patient-engaging surfaces 712, 714, 716 can include contours, shapes, and the like that are substantially complementary or mirror images of the bone portions of the patient (for example, the patient's pelvis). While the illustrated example depicts three arms 718, 720, 722, three adjustable fingers 706, 708, 710, and three patient-engaging surfaces 712, 714, 716, in other examples, the alignment plate 700 can comprise more than three or less than three arms 718, 720, 722, fingers 706, 708, 710, or patient-engaging surfaces 712, 714, 716.

The distances 728, 730, 732 between the patient-engaging surfaces 712, 714, 716 and the implant-facing surface 726 can be adjusted via the adjustable fingers 706, 708, 710 to control an inclination and anteversion angle of an implant. In at least one example, the alignment plate 700 can comprise one or more indicators to indicate to a user the position of each adjustable finger 706, 708, 710. In some examples, the user can select a preselected position of each adjustable finger 706, 708, 710 based on software, patient images, or other surgical plan information. In at least one example, the preselected position corresponds to the indicator, such that the user can verify that each of the adjustable fingers 706, 708, 710 is in the preselected position based on the indicator.

In at least one example, each adjustable finger 706, 708, 710 can comprise an adjustment interval corresponding to a particular increase or decrease of implant inclination angle or anteversion angle. In at least one example, the alignment plate 700 can be configured to allow the user to make inter-operative adjustments from the preselected position and still have a reference for the inclination and anteversion angle. The alignment plate can also include features to reference anatomical landmarks on the patient's anatomy that will aid with alignment. The alignment plate 700 can allow a user to implement a surgical plan with minimal deviation from traditional procedures (e.g. Total Hip Arthroplasty (THA)), requiring minimal soft tissue clearance, and reducing time registering to the unique patient anatomy. The one or more adjustable fingers 706, 708, 710 can additionally allow the user to make intra-operative adjustments to the surgical plan. Further, the alignment plate 700 can facilitate precise guide registration because it does not rely on segmentation data from the fossa region of the acetabulum. The adjustability of the alignment plate 700 can allow the alignment plate 700 to be re-used for multiple patients, reducing or altogether removing lead time between when a user creates a surgical plan and when the alignment plate 700 is available for the surgical plan.

Figure 8:
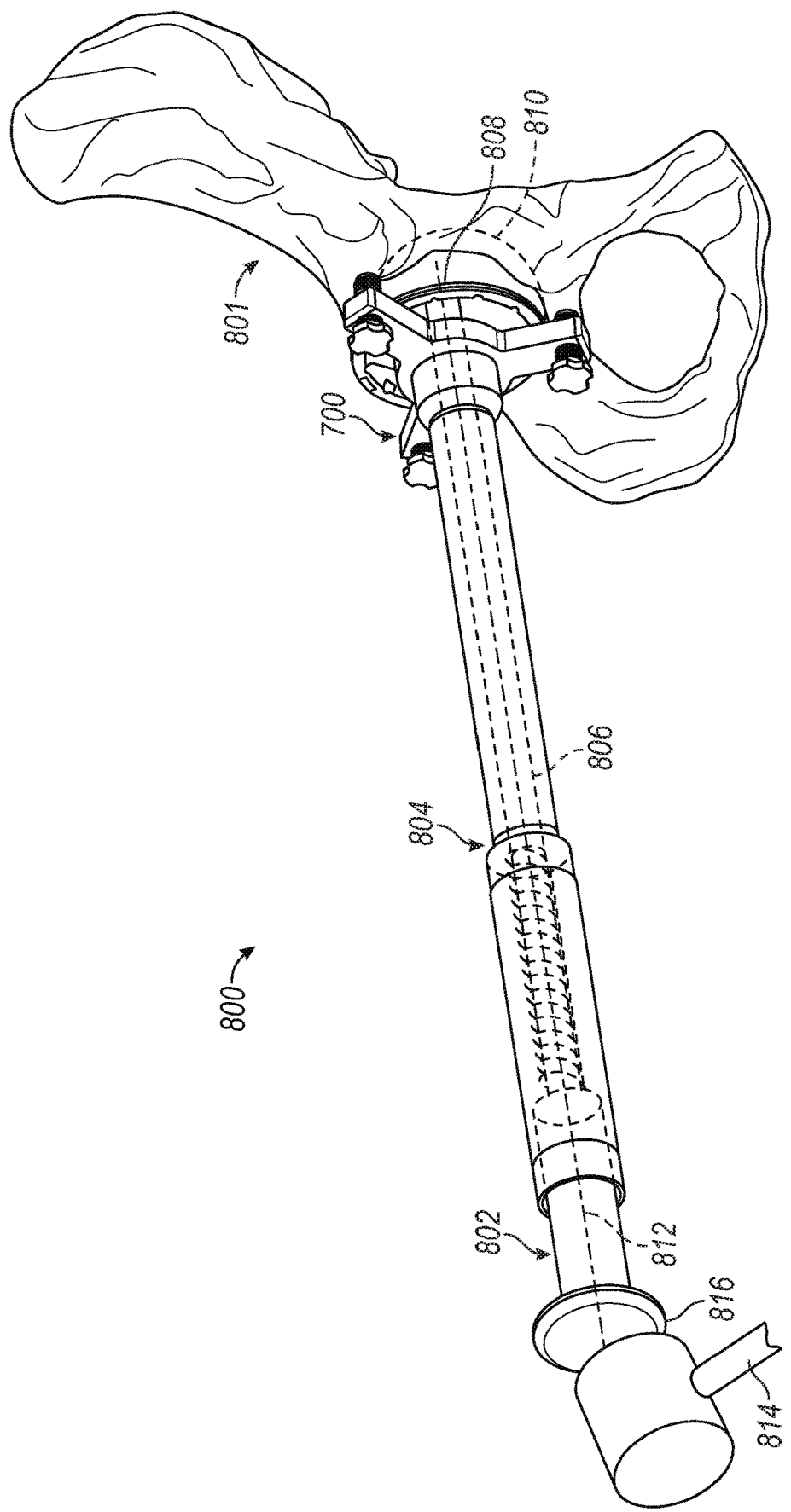
FIG. 8 is an environmental view of an alignment system, in accordance with at least one example of the present disclosure.

FIG. 8 is an environmental view of an alignment system 800 with relation to a portion of a patient's anatomy 801, in accordance with at least one example of the present disclosure. While in the illustrated example, the alignment system 800 is depicted in use with a patient's pelvis 801, in other examples, the alignment system 800 can be used in different portions of a patient's anatomy.

The alignment system 800 can include a sleeve 804 having a through bore 806 (extending at least partially through the sleeve 804) and the alignment plate 700 of FIG. 7. In the illustrated example, the alignment system 800 can additionally include an implant 808 (in the illustrated example, an acetabular cup 808) and an impaction rod 802. The alignment system 800 can be assembled such that the impaction rod 802 can be passed through the sleeve 804, such as passing the impaction rod 802 through the through bore 806 of the sleeve 804 and through the alignment plate 700 to engage the acetabular cup 808. The alignment plate 700 can be threaded or otherwise couple to the sleeve 804 prior to passing the impaction rod 802 through the sleeve 804 to engage the acetabular cup 808. In at least one example, the rod 802 can be configured to be attached to the acetabular cup 808 after the assembly of the sleeve 804 to the alignment plate 700 and passing the rod 802 through the sleeve 804 and plate 700.

Once assembled, the patient-engaging surfaces 712, 714, 716 of the alignment plate 700 can engage the selected boney portions of the patient's anatomy 801 near or adjacent the implant site 810 (in the illustrated example, the pelvis 801 near or adjacent to the acetabulum 810). The alignment plate 700 can align an axis 812 with a preselected orientation by engaging the boney portions adjacent to the acetabulum 810. As illustrated in FIG. 5, the indicator 24a may be provided and/or used to assist in at least initial alignment of the alignment plate 700 with the pelvis 801 and the selected boney portions. The adjustable fingers 706, 708, 710 can be configured to be adjusted such that the patient-engaging surfaces 712, 714, 716 contact the boney portions to align the axis 812 relative to the acetabulum 810 as preselected prior to the procedure. As such, the acetabular cup 808 can be appropriately aligned within the acetabulum 810 prior to impaction of the acetabular cup 808 into the acetabulum 810.

Once appropriately aligned, a mallet 814 can be used to engage in a selected manner, such as a forceful manner, the impaction rod 802. For example, the mallet 814 can strike or otherwise impact an impaction head 816 of the impaction rod 802. By impacting the impaction rod 802, the acetabular cup 808 can be engaged into the acetabulum 810. Various acetabular cups can be impacted into the acetabulum 810, for example, substantially cementless acetabular cups. In some examples, various cements can be positioned in the acetabulum 810 prior to impaction. In some examples, the cup 808 can be held in the acetabulum 810 by a cement material and impaction with the mallet 814 may not be required. In an example of a cemented system, the cup 808 can be placed in a cement mantle and the system 800 can be used for alignment purposes rather than also providing the rod 801 for a forceful impaction of the cup 808.

Accordingly, once the acetabular cup 808 is implanted, such as by placement and/or impaction in the acetabulum 810, the impaction rod 802 can be disengaged from the acetabular cup 808, for example by unthreading the impaction rod 802 from the acetabular cup 808. Once the impaction rod 802 is disengaged from the acetabular cup 808, the sleeve 804 and the alignment plate 700 are free to be removed from contact with the pelvis 801. Accordingly, the acetabular cup 808 can be implanted in a preselected alignment and orientation within the acetabulum 810 based upon the distances 728, 730, 732 between the patient-engaging surfaces 712, 714, 716 and the implant-facing surface 726, as discussed above.

While the illustrated example depicts an implant 808 and an impaction rod 802, the sleeve 804 and the alignment plate 700 can be used with a reaming tool to align the reaming tool during reaming procedures.

Figure 9:
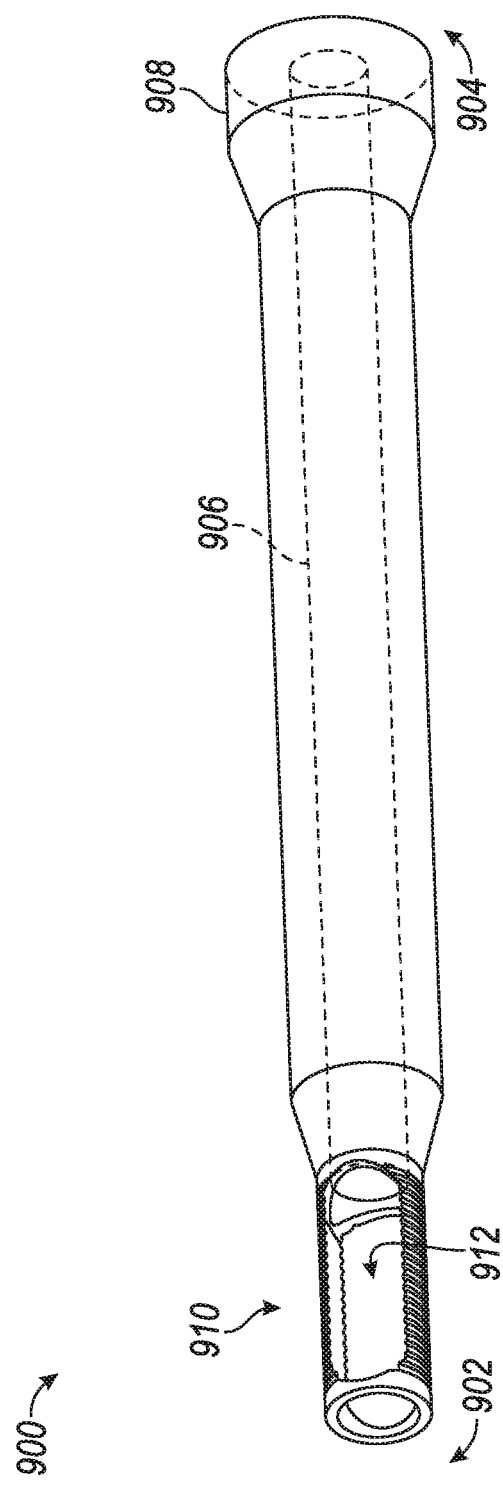
FIG. 9 is a plan view of a sleeve member, in accordance with at least one example of the present disclosure.

FIG. 9 is a plan view of a sleeve member 900, in accordance with at least one example of the present disclosure. The sleeve member 900 can generally include a first end 902, a second end 904, and a through bore 906 extending at least partially through the sleeve member 900. In at least one example, the through bore 906 can extend through the sleeve member 900 from the first end 902 to the second end 904. The through bore 902 can be configured to slidably receive a rod, such as an impaction rod, a reaming tool rod, or the like. In the illustrated example, the sleeve member 900 can include an alignment plate-engaging portion 908 at the second end 904 to hold an alignment plate (such as the example alignment plates discussed with reference to FIGS. 1-8) relative to the sleeve member 900 during movement of the rod.

In some examples, the sleeve member 900 can include a depth control portion 910, for example, a depth indicator or a depth stop instrument to prevent a reamer tool from reaming beyond a selected depth. In the illustrated example, the depth control portion 910 can provide a depth indicator in the form of a window 912. In some examples, the depth control portion 910 can include markings to indicate the ream depth. In at least one example, the rod can include markings to indicate the ream depth. In some examples, the depth control portion 910 can be configured to be manipulated by a user based on a surgical plan or other preselected reaming depth. In at least one example the depth control portion 910 can be adjustable to allow for a variety of selected depths (e.g., a threaded member that can be rotated to increase or decrease a selected depth reaming amount).

The depth control portion 910 can allow a user to plan or reference reaming depth, and accurately recreate the planned reaming depth and make intra-operative adjustments if necessary. In at least one example, a software or patient image can indicate parameters associated with ream depth.

Figure 10A:
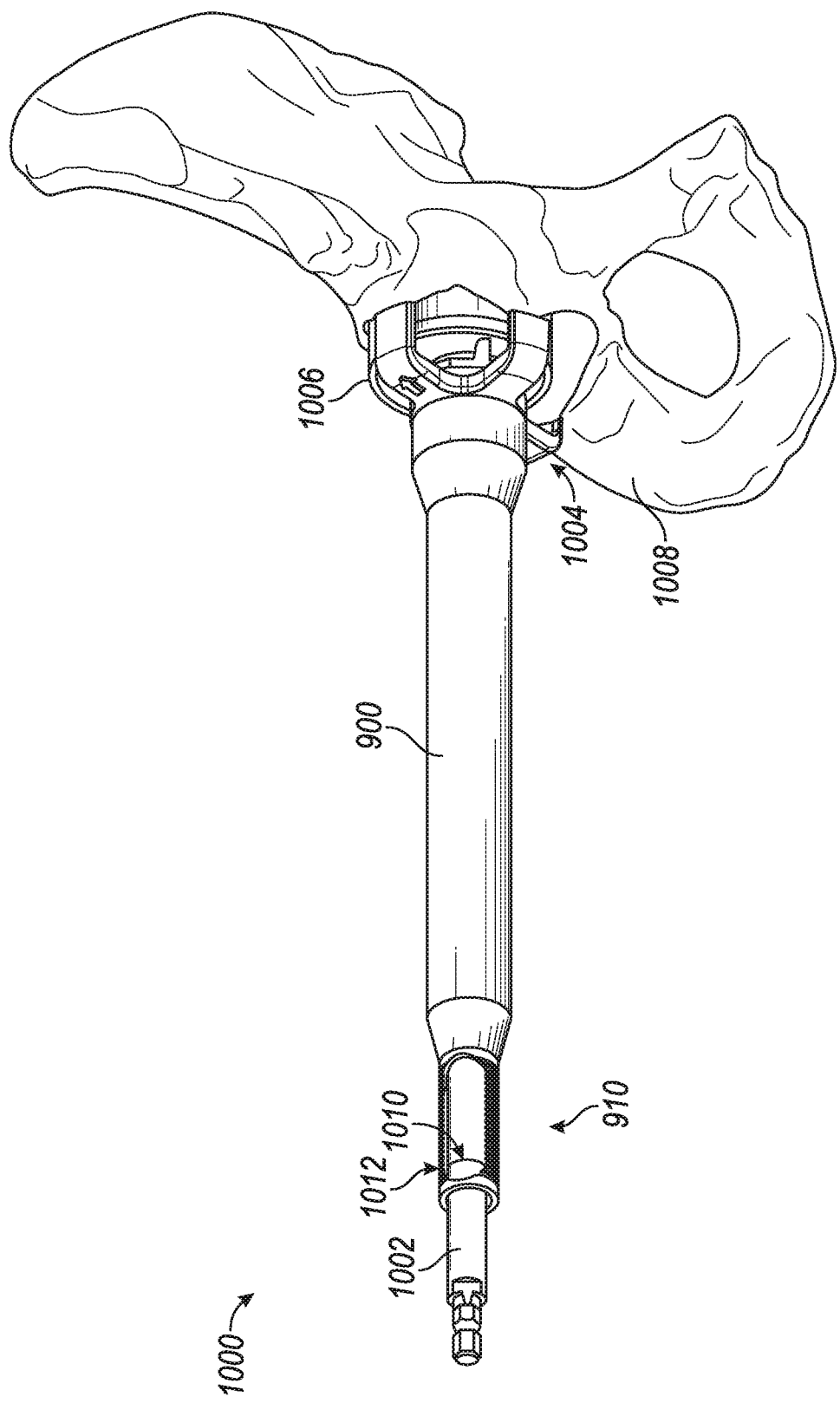
FIG. 10A is an environmental view of the sleeve member of FIG. 9 associated with a first depth, in accordance with at least one example of the present disclosure.
Figure 10B:
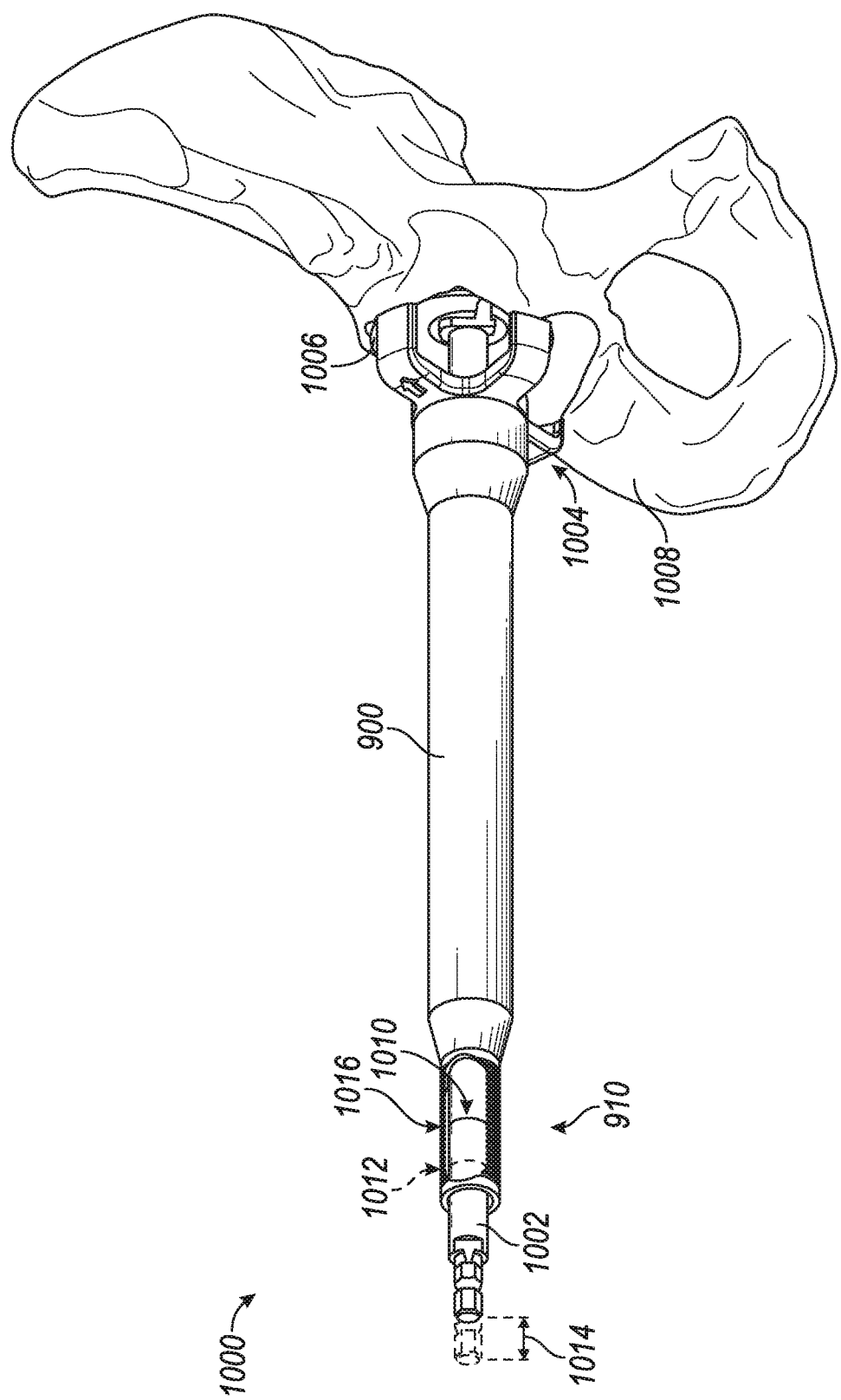
FIG. 10B is an environmental view of the sleeve member of FIG. 9 associated with a second depth, in accordance with at least one example of the present disclosure.

FIGS. 10A and 10B are environmental views of an alignment system 1000 including the sleeve member 900 of FIG. 9 at different reaming depths, in accordance with some examples of the present disclosure. In the illustrated example, the alignment system 1000 can include the sleeve member 900, a rod 1002, and an alignment plate 1004. The alignment plate 1004 can include any one or more features of the alignment plate examples described with reference to FIGS. 1-8. In the illustrated example, the sleeve member 900 can be used with a reaming tool rod 1002 and a reamer 1006 to ream a patient's anatomy 1008 to a preselected depth.

The depth control portion 910 of the sleeve member 900 can indicate the location of a rod marking 1010 relative to markings or other indicators on the depth control portion 910 to indicate a reaming depth relative to the preselected reaming depth. In FIG. 10A, the rod marking 1010 can be positioned at indicator 1012 of the depth control portion 910.

In FIG. 10B, the rod 1002 has advanced as the reamer 1006 reams further into the patient's anatomy 1008. The distance 1014 traveled by the rod is associated with the reaming depth and is indicated by the change in the position of the rod marking 1010 from position 1012 to position 1016 relative to the depth control portion. In some examples, the depth control portion 910 can include markings to indicate depth intervals. In at least one example, the depth control portion 910 can include an arrow or other marker indicating the preselected depth. In some examples, the depth control portion 910 can include a depth stop instrument to prevent the rod 1002 from advancing beyond a selected distance associated with a preselected depth. In at least one example, the user can adjust the depth stop instrument based on the preselected depth.

While the examples illustrated in FIGS. 9-10B are generally described with reference to reaming depth, the sleeve member 900 can similarly be used to indicate a depth of impaction. In at least one example, a depth of impaction of an implant can be preselected, and the depth control portion 910 of the sleeve member 900 can be used to indicate the depth of the implant relative to the preselected depth.

In the foregoing Detailed Description, it can be seen that various features are grouped together in a single example for the purpose of streamlining the disclosure. This method of disclosure is not to be interpreted as reflecting an intention that the claimed examples require more features than are expressly recited in each claim. Rather, as the following claims reflect, inventive subject matter lies in less than all features of a single disclosed example. Thus the following claims are hereby incorporated into the Detailed Description, with each claim standing on its own as a separate example.

Note that not all of the activities or elements described above in the general description are required, that a portion of a specific activity or device may not be required, and that one or more further activities may be performed, or elements included, in addition to those described. Still further, the order in which activities are listed are not necessarily the order in which they are performed. Also, the concepts have been described with reference to specific examples. However, one of ordinary skill in the art appreciates that various modifications and changes can be made without departing from the scope of the present disclosure as set forth in the claims below. Accordingly, the specification and figures are to be regarded in an illustrative rather than a restrictive sense, and all such modifications are intended to be included within the scope of the present disclosure.

Benefits, other advantages, and solutions to problems have been described above with regard to specific examples. However, the benefits, advantages, solutions to problems, and any feature(s) that may cause any benefit, advantage, or solution to occur or become more pronounced are not to be construed as a critical, required, or essential feature of any or all the claims. Moreover, the particular examples disclosed above are illustrative only, as the disclosed subject matter may be modified and practiced in different but equivalent manners apparent to those skilled in the art having the benefit of the teachings herein. No limitations are intended to the details of construction or design herein shown, other than as described in the claims below. It is therefore evident that the particular examples disclosed above may be altered or modified and all such variations are considered within the scope of the disclosed subject matter. Accordingly, the protection sought herein is as set forth in the claims below.

What is claimed is:

1. A system for placement of an implant in a predetermined orientation, comprising:
   a rod extending from a first end to a second end;
   a sleeve member extending from a proximal end to a distal end having a through bore extending through the sleeve member configured to slidably receive the rod; and
   an alignment plate, comprising:
      a body having an exterior-facing surface and an implant-facing surface;
      a through bore extending at least partially through the body, the rod configured to extend through the through bore;
      at least one adjustable finger extending in a direction transverse to a plane defined by the body; and
      at least one patient-engaging surface positioned on the at least one adjustable finger, the at least one patient-engaging surface structured to be spaced radially outward of the implant and also spaced radially from the body, wherein the adjustable finger is adjustable to vary the distance between the patient-engaging surface and the implant-facing surface, wherein the patient-engaging surface is configured to engage a portion of a patient during placement of the implant to align the alignment plate relative to the patient in the predetermined orientation, wherein the patient-engaging surface is adjustable in a direction transverse to a plane defined by the body from a first position to a second position, such that the patient-engaging surface is configured to engage the portion of the patient in the second position,
   wherein the distal end of the sleeve is configured to terminate at the alignment plate for placement of the implant.

2. The system of claim 1, wherein the predetermined orientation is selected based on image data of the patient.

3. The system of claim 1, further comprising at least one threaded hole extending at least partially through the body, wherein the at least one adjustable finger comprises a threaded member that is configured to threadably engage the at least one threaded hole to vary the distance between the patient-engaging surface and the implant-facing surface by rotation of the at least one adjustable finger in a clockwise direction or a counterclockwise direction.

4. The system of claim 3, wherein the body comprises:
   a central region; and
   at least one arm extending radially outward from the central region, wherein the at least one threaded hole extends at least partially through the at least one arm.

5. The system of claim 4, wherein the at least one finger is adjustable in an orthogonal direction relative to the at least one arm.

6. The system of claim 1, wherein the at least one adjustable finger comprises at least three adjustable fingers.

7. The system of claim 1, further comprising:
   a sleeve member extending from a first end to a second end having a through bore extending through the sleeve and configured to receive the rod;
   wherein the sleeve member further includes an alignment plate-engaging portion at the second end to hold the alignment plate relative to the sleeve member during movement of the rod.

8. A system, comprising:
   a rod extending from a first end to a second end;
   a sleeve member extending from a proximal end to a distal end having a through bore extending through the sleeve member configured to slidably receive the rod; and
   an alignment plate configured to place an implant in a patient in a predetermined orientation, the alignment plate having:
      a central region;
      a through bore extending at least partially through the central region, the rod configured to extend through the through bore; and
      at least one engaging surface structured to be spaced radially outward of the implant and also spaced radially from the central region, the engaging surface configured to engage a portion of a patient while placing the implant to align the alignment plate and the rod relative to the patient, wherein the at least one engaging surface is adjustable in a direction transverse to the central region from a first position to a second position, such that the engaging surface is configured to engage the portion of the patient in the second position,
   wherein the distal end of the sleeve is configured to terminate at the alignment plate for placement of the implant.

9. The system of claim 8, wherein the sleeve member further includes an alignment plate-engaging portion at the distal end to hold the alignment plate relative to the sleeve member during movement of the rod.

10. The system of claim 9, wherein the rod comprises part of a reamer tool and the sleeve member comprises a depth indicator.

11. The system of claim 9, wherein the rod comprises part of a reamer tool and the sleeve member comprises a depth stop instrument to prevent the reamer tool from reaming beyond a selected depth.

12. The system of claim 11, wherein the depth stop instrument is adjustable to allow for a variety of selected depths.

13. The system of claim 8, further comprising:
at least one adjustable finger extending radially from the central region, the at least one adjustable finger adjustable to vary the distance between the at least one engaging surface and the central region in the direction transverse to the central region.

14. The system of claim 13, wherein:
the at least one adjustable finger comprises at least three adjustable fingers;
the at least one engaging surface comprises at least three engaging surfaces;
each of the at least three fingers has at least one of the engaging surfaces; and
each of the engaging surfaces is configured to selectively engage a portion of the patient during positioning of an implant with the rod.

15. A system for placing a prosthetic member, comprising:
a rod extending from a first rod end to a second rod end;
a sleeve extending from a first sleeve end to a second sleeve end having a through bore extending through the sleeve configured to slidably receive the rod member; and
an alignment plate having:
a through bore through which the rod is configured to extend;
a first arm and a second arm both extending from a central region through which the through bore extends;
a first finger including a first patient-engaging surface configured to be spaced a first distance in a transverse direction from the first arm, the first finger extending along its length from the first arm to the first patient-engaging surface, wherein the first patient-engaging surface is adjustable in a direction transverse to the central region from a first position to a second position, such that the engaging surface is configured to engage the portion of the patient in the second position; and
a second finger including a second patient-engaging surface configured to be spaced a second distance in a transverse direction from the second arm, the second finger extending along its length from the second arm to the second patient-engaging surface, wherein the second distance is different than the first distance;
wherein the first distance and the second distance are selected to achieve a preselected alignment of at least one of the rod or the sleeve when the sleeve is engaged to the alignment plate and the first patient-engaging surface and the second patient-engaging surface are engaging the subject,
wherein the second sleeve end is a distal end of the sleeve, and the distal end of the sleeve is configured to terminate at the alignment plate for placement of the prosthetic member.

16. The system of claim 15, wherein the sleeve further includes an alignment plate-engaging portion at the distal end, such that the sleeve is configured to be coupled to the alignment plate to hold the alignment plate relative to the sleeve member during movement of the rod, wherein the rod is configured to slide relative to the alignment plate.

17. The system of claim 15, wherein the alignment plate further includes
a third arm extending from the central region, wherein the third arm is spaced a distance from each of the first and second arms around the central region; and
a third adjustable patient-engaging surface configured to be positioned a third distance in a transverse direction from the third arm.

18. The system of claim 15, wherein:
the first finger extends between the first arm and the first adjustable patient-engaging surface; and
the second finger extends between the second arm and the second adjustable patient-engaging surface.

19. The system of claim 18, wherein the first finger is configured to move the first adjustable patient-engaging surface closer to and further from the first arm, and the second finger is configured to move the second adjustable patient-engaging surface closer to and further from the second arm.

20. The system of claim 19, wherein the first finger comprises a first threaded member configured to engage a first threaded hole extending through the first arm, and the second finger comprises a second threaded member configured to engage a second threaded hole extending through the second arm.

* * * * *